(12) United States Patent
Shin et al.

(10) Patent No.: US 7,993,410 B2
(45) Date of Patent: Aug. 9, 2011

(54) ESOPHAGEAL STENT

(75) Inventors: Kyong-Min Shin, Seoul (KR);
Jin-Hong Kim, Kyunggi-do (KR);
Mizumoto Yoshinori, Fushimi-ku (JP)

(73) Assignee: Taewoong Medical Co., Ltd., Kyunggi-Do (KR)

( * ) Notice: Subject to any disclaimer, the term of this patent is extended or adjusted under 35 U.S.C. 154(b) by 463 days.

(21) Appl. No.: 11/330,595

(22) Filed: Jan. 12, 2006

(65) Prior Publication Data
US 2006/0212052 A1   Sep. 21, 2006

(30) Foreign Application Priority Data
Mar. 21, 2005  (KR) .................. 10-2005-0023339

(51) Int. Cl.
*A61F 2/24* (2006.01)
*A61F 2/04* (2006.01)

(52) U.S. Cl. .................................. 623/23.68; 623/2.14
(58) Field of Classification Search .................. 606/151, 606/153; 623/1.12, 1.13, 1.16, 1.24, 1.25, 623/1.26, 1.28, 2.1, 2.14, 2.18, 23.65–23.71
See application file for complete search history.

(56) References Cited

U.S. PATENT DOCUMENTS

| 5,861,036 | A | | 1/1999 | Godin | |
|---|---|---|---|---|---|
| 6,126,686 | A | * | 10/2000 | Badylak et al. | 623/1.24 |
| 6,156,064 | A | * | 12/2000 | Chouinard | 623/1.44 |
| 6,302,917 | B1 | * | 10/2001 | Dua et al. | 623/23.68 |
| 6,764,518 | B2 | * | 7/2004 | Godin | 623/23.68 |
| 2001/0021872 | A1 | * | 9/2001 | Bailey et al. | 623/1.24 |

FOREIGN PATENT DOCUMENTS

JP    10-211287    8/1998

* cited by examiner

*Primary Examiner* — Darwin P Erezo
*Assistant Examiner* — Dianne Dornbusch
(74) *Attorney, Agent, or Firm* — Jordan and Hamburg LLP

(57) ABSTRACT

Disclosed is an esophageal stent placed in a stenosed part of the esophagus having a flexible tube to prevent the reverse flow of gastric contents from the stomach is coupled to the lower end of the esophageal stent. The flexible tube has an inside membrane and an outside membrane adhered to each other, thus having a twofold structure with at least one core longitudinally placed between the adhered inside and outside membranes while the core extends from the upper end toward the lower end of the flexible tube. Thus, the flexible tube is prevented from being inverted, and prevents the reverse flow of the gastric contents, and maximizes the operational reliability of the esophageal stent. The flexible tube does not cause a patient pain or discomfort due to frictional contact of the tube with the inner surface of the stomach when the tube moves in the stomach.

14 Claims, 9 Drawing Sheets

Related Art

Related Art

ESOPHAGEAL STENT

BACKGROUND OF THE INVENTION

The present invention relates generally to an esophageal stent to be placed in a stenosed part of the esophagus or gullet, which communicates with the stomach, thus enlarging the size of the passage of the stenosed part and making swallowing easier and, more particularly, to an esophageal stent which has a flexible tube coupled to the lower end of the esophageal stent such that the flexible tube is placed in the stomach and prevents reverse flow of gastric contents from the stomach, with an elastic core being set in the flexible tube and preventing inversion of the tube, thus efficiently preventing the gastric contents from reversely flowing from the stomach.

The esophagus, or gullet, may be narrowed and, furthermore, blocked by stenosis caused by cancer, and, in the related art, such stenosed part of the gullet may be treated by surgery. However, surgery to the stenosed gullet causes pain to the patient and, furthermore, surgery is not as effective as desired.

Thus, in recent years, a self-expandable esophageal stent has been proposed and used, which has a hollow cylindrical mesh structure fabricated by weaving shape-memory alloy wires and is inserted into a lesioned part, or stenosed part of the gullet, thus being placed at the lesioned part and enlarging the size of the stenosed passage of the lesioned part. The self-expandable esophageal stent is advantageous in that, once the stent is placed at the lesioned part of the stenosed gullet, the stent can be used semi-permanently.

To place the self-expandable esophageal stent at a lesioned part of the stenosed gullet, an operator primarily shrinks the stent so as to reduce the volume of the stent, installs the shrunken stent in a stent insertion device, and inserts the stent into the stenosed part of the gullet using the insertion device. After the stent reaches the stenosed part of the gullet, the stent is pushed so that the stent, fabricated from shape-memory alloy wires, is separated from the insertion device and elastically expands and restores its original shape, thus pushing the wall of the stenosed part outwards in radial directions and thereby enlarging the size of the passage of the stenosed part, making swallowing easier.

However, when the gullet is stenosed in its lower end, at which the gullet communicates with the stomach where the esophageal sphincter is located to close or open the junction between the gullet and the stomach, the esophageal stent must be placed in the lower end of the gullet so that the stent always opens the esophageal sphincter as well as the stenosed part so that the lower end of the gullet is always opened and communicates with the stomach.

Thus, when the conventional esophageal stent is placed in the stenosed lower end of the gullet, the esophageal sphincter of the stenosed lower end of the gullet is always opened by the stent. Therefore, the conventional esophageal stent placed in the stenosed lower end of the gullet always opens the stomach and causes the gastric contents to flow reversely from the stomach through the gullet.

In an effort to overcome the above-mentioned problem, U.S. Pat. Nos. 5,861,036 and 6,302,917 B1, and Japanese Patent No. Hei. 9-32933 each disclose a technique of preventing reverse flow of gastric contents, in which a flexible tube is coupled to the lower end of the stent such that the flexible tube is placed in the stomach when the stent is set in a lesioned part of the gullet, thus causing the flexible tube to act as a check valve.

Described in detail, as shown in FIGS. 1 and 2, flexible reverse flow prevention tube 5 to prevent the reverse flow of gastric contents from the stomach 7 is coupled to a hollow stent body 3 having a mesh structure fabricated by weaving superelastic shape-memory alloy wires. The stent body 3 having the flexible tube 5 is inserted into and is placed in a stenosed part 9 of the gullet 8 such that the stent body 3 enlarges the size of the stenosed part 9 and makes swallowing easier, with the flexible tube 5 being placed in the stomach 7.

Therefore, food can be smoothly and safely swallowed from the mouth down to the stomach 7 through both the stent body 3 and the flexible reverse flow prevention tube 5, while the flexible tube 5 prevents gastric contents from reversely flowing into the gullet 8.

However, the conventional reverse flow prevention tube 5 provided on the esophageal stent is problematic as follows. Described in detail, the tube 5, made of a flexible material, may move within the stomach 7 while coming into frictional contact with the inner surface of the stomach 7, so that the tube 5 may cause pain and discomfort to a patient.

Furthermore, when the patient clears his/her throat or is nauseous, pressure may act in the tube 5 so that the reverse flow prevention tube 5 may be inverted into the hollow stent body 3. In the above state, gastric contents may flow reversely from the stomach 7 through the inverted tube 5.

Furthermore, the conventional esophageal stent placed in the stenosed gullet may move from a designated part of the gullet due to pressure caused by contact of the stent with food flowing from the mouth down to the stomach through the gullet. Thus, in an effort to overcome the problem of undesired movement of the stent in the designated part of the gullet, an enlarged diameter part may be provided on each end of the stent so that the stent can be caught and reliably maintained in the designated part of the gullet. In addition, the conventional esophageal stent has a mesh structure fabricated by weaving the shape-memory alloy wires, so that the lesioned part of the gullet, enlarged by the stent, come into contact with food flowing from the mouth down to the stomach through the gullet. Thus, the patient feels pain. In an effort to prevent the patient from feeling pain, the stent may be provided with a coating layer or an artificial membrane which isolates the lesioned part of the gullet from flowing food.

Furthermore, in the related art, an esophageal stent, which has reverse flow prevention tube 5, as well as the enlarged diameter parts, the coating layer, or the artificial membrane, has been proposed and used. However, the stent has the same problem experienced with conventional esophageal stents.

BRIEF SUMMARY OF THE INVENTION

Accordingly, the present invention has been made keeping in mind the above problems occurring in the prior art, and an object of the present invention is to provide an esophageal stent, in which a flexible tube, coupled to the lower end of the esophageal stent and preventing the reverse flow of gastric contents from the stomach, is configured such that the tube is prevented from being inverted in any circumstances, and which thus prevents the reverse flow of the gastric contents and maximizes the operational reliability of the esophageal stent.

Another object of the present invention is to provide an esophageal stent, in which the flexible tube coupled to the lower end of the esophageal stent is configured such that the flexible tube does not cause a patient pain or discomfort due to frictional contact of the tube with the inner surface of the stomach when the tube moves in the stomach.

In order to accomplish the above object, the present invention provides an esophageal stent comprising a stent body, having a hollow cylindrical mesh structure fabricated by weaving superelastic shape-memory alloy wires, and a flexible reverse flow prevention tube coupled to the lower end of the stent body and preventing the reverse flow of gastric contents, wherein the flexible reverse flow prevention tube comprises an inside membrane and an outside membrane adhered to each other, thus having a twofold structure with at least one core longitudinally placed between the adhered inside and outside membranes while the core extends from an upper end toward a lower end of the flexible tube. In the esophageal stent, the core extends from the upper end of the flexible reverse flow prevention tube a distance of at least half of the length (1) of the flexible tube.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
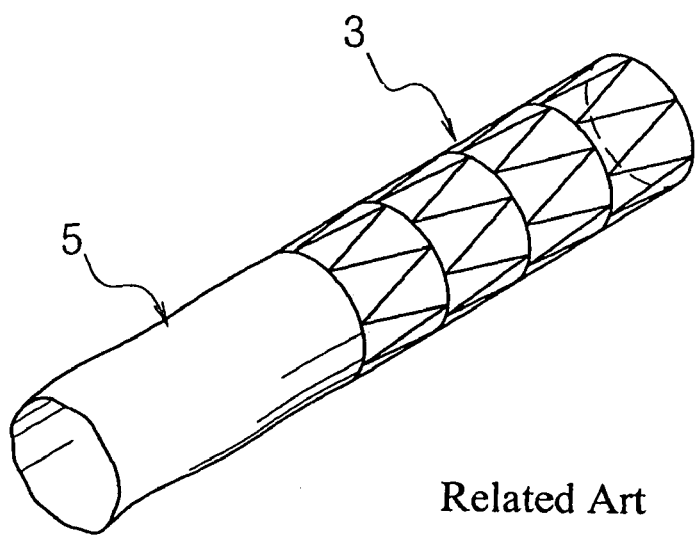
FIG. 1 is a perspective view illustrating the construction of a conventional esophageal stent.
Figure 2:
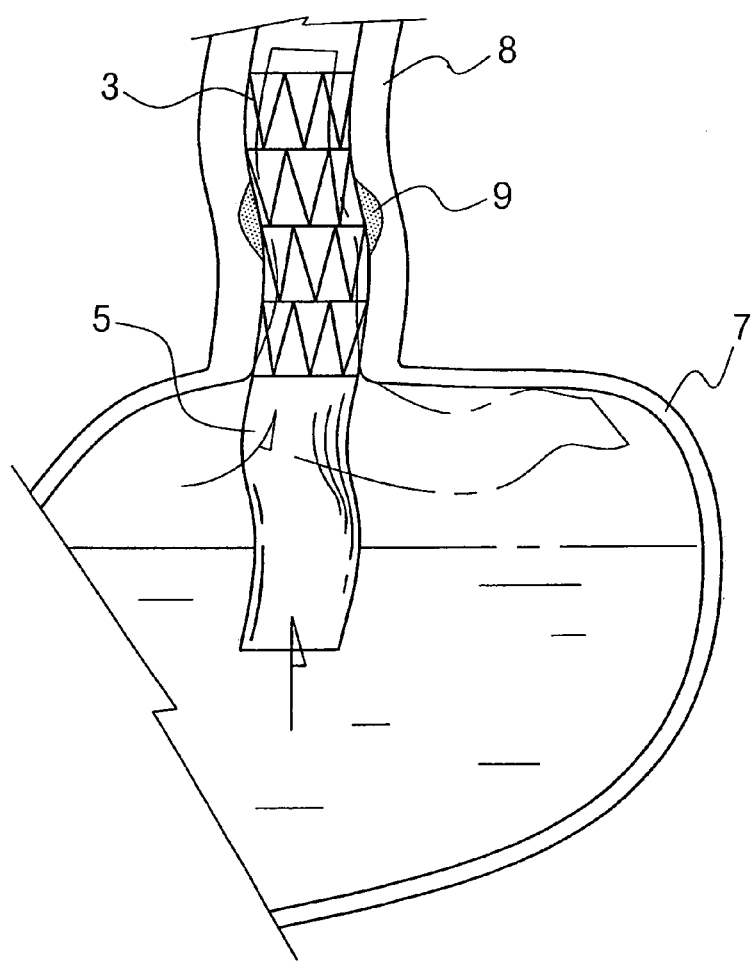
FIG. 2 is a view illustrating the stent of FIG. 1 which is placed in the lower end of the gullet, which communicates with the stomach.

Reference now should be made to the drawings, in which the same reference numerals are used throughout the different drawings to designate the same or similar components.

Figure 3:
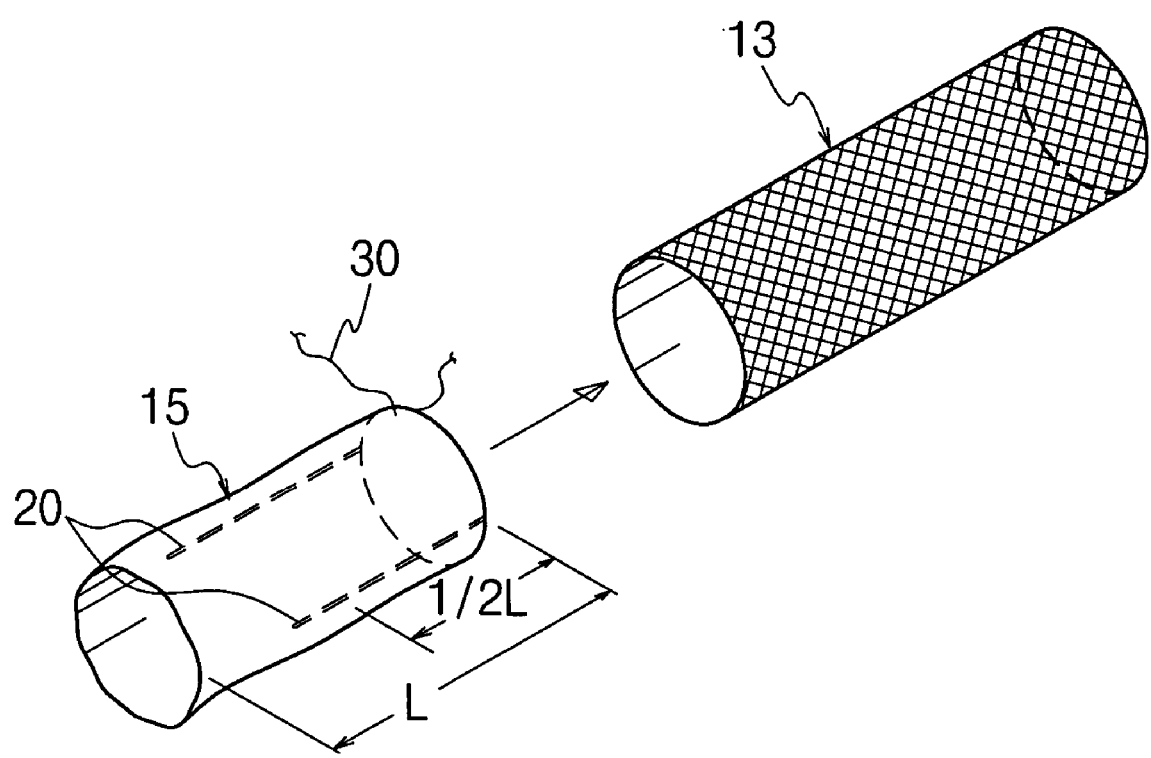
FIG. 3 is an exploded perspective view illustrating the construction of an esophageal stent according to a first embodiment of the present invention.
Figure 4:
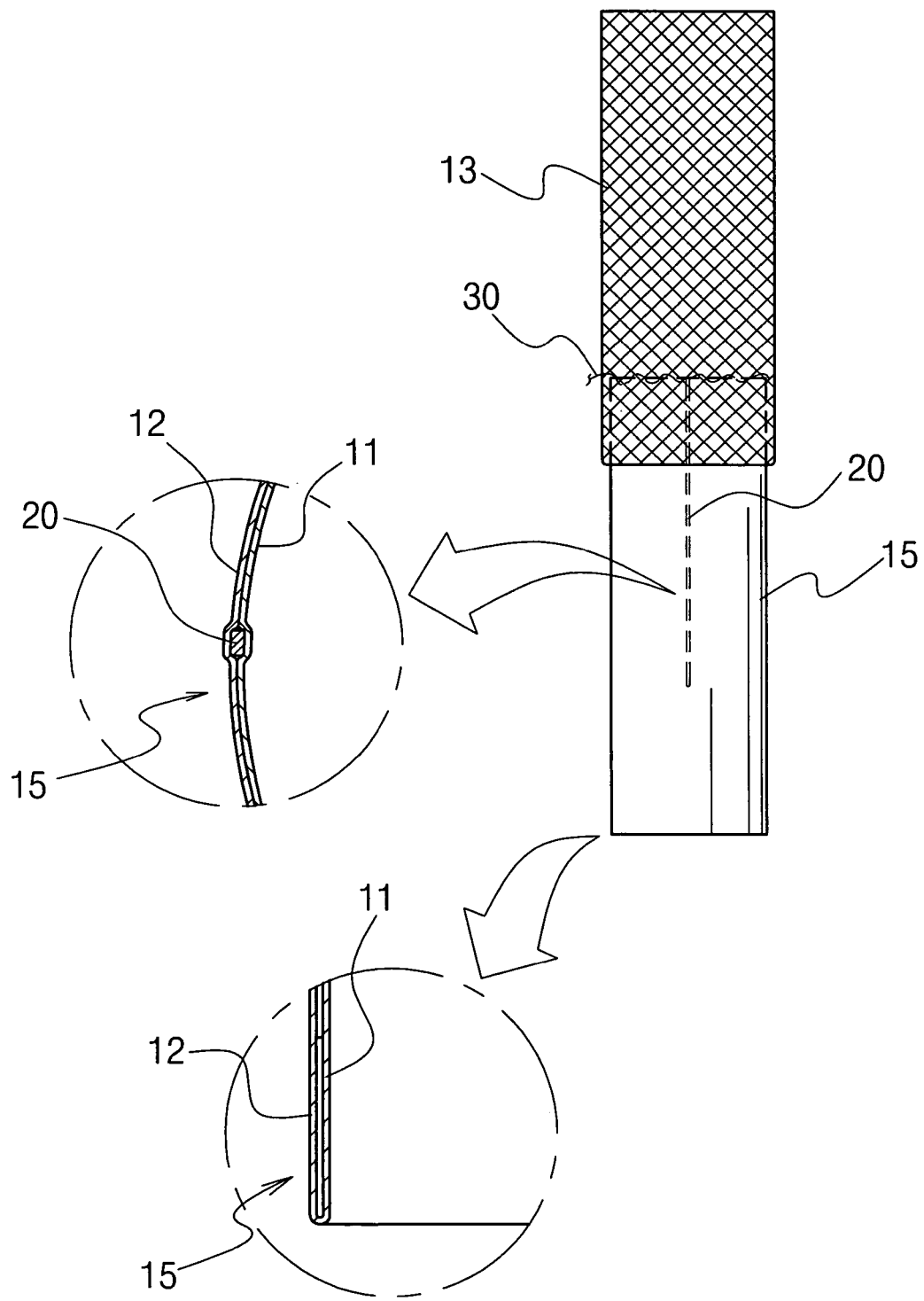
FIG. 4 is a front view illustrating the assembled stent of FIG. 3.

As shown in FIGS. 3 and 4, the esophageal stent according to the present invention comprises a stent body 13, having a hollow cylindrical mesh structure fabricated by weaving superelastic shape-memory alloy wires, and a flexible reverse flow prevention tube 15 coupled to the lower end of the stent body 13 and preventing the reverse flow of gastric contents.

In the esophageal stent, the flexible reverse flow prevention tube 15 comprises an inside membrane 11 and an outside membrane 12 adhered to each other, thus having a twofold structure with at least one core 20 longitudinally placed between the adhered inside and outside membranes 11 and 12 while the core extends from the upper end toward the lower end of the flexible tube 15.

In the present invention, the flexible reverse flow prevention tube 15 is preferably made of PTFE (Polytetra fluoroethylene) which is benign to the human body. To produce the flexible tube 15, the inside and outside membranes 11 and 12 may be made of a single membrane by inwardly and inversely folding the lower end of the single membrane, thus providing the inside and outside membranes 11 and 12. Alternatively, the flexible tube 15 may be produced by fitting an outside membrane 12 over an inside membrane 11.

Particularly, the flexible tube, which has the inside and outside membranes made of a single membrane by inwardly and inversely folding the lower end of the single membrane, thus providing the inside and outside membranes, is preferred over the flexible tube produced by fitting the outside membrane over the inside membrane, because the folding process is easier than the fitting process and the folded single membrane provides a rounded junction between the lower ends of the inside and outside membranes.

In the present invention, two or three cores 20, each preferably made of an elastic alloy, preferably extend from the upper end of the flexible reverse flow prevention tube 15 a distance of at least half of the length (1) of the flexible tube 15.

To couple the flexible reverse flow prevention tube 15 to the stent body 13, the upper end of the tube 15 may be stitched to the inside part or the lower end of the stent body 13 using a thread 30, as shown in the drawing. Alternatively, the tube 15 may be adhered to the stent body 13 using a bonding agent.

Figure 8:
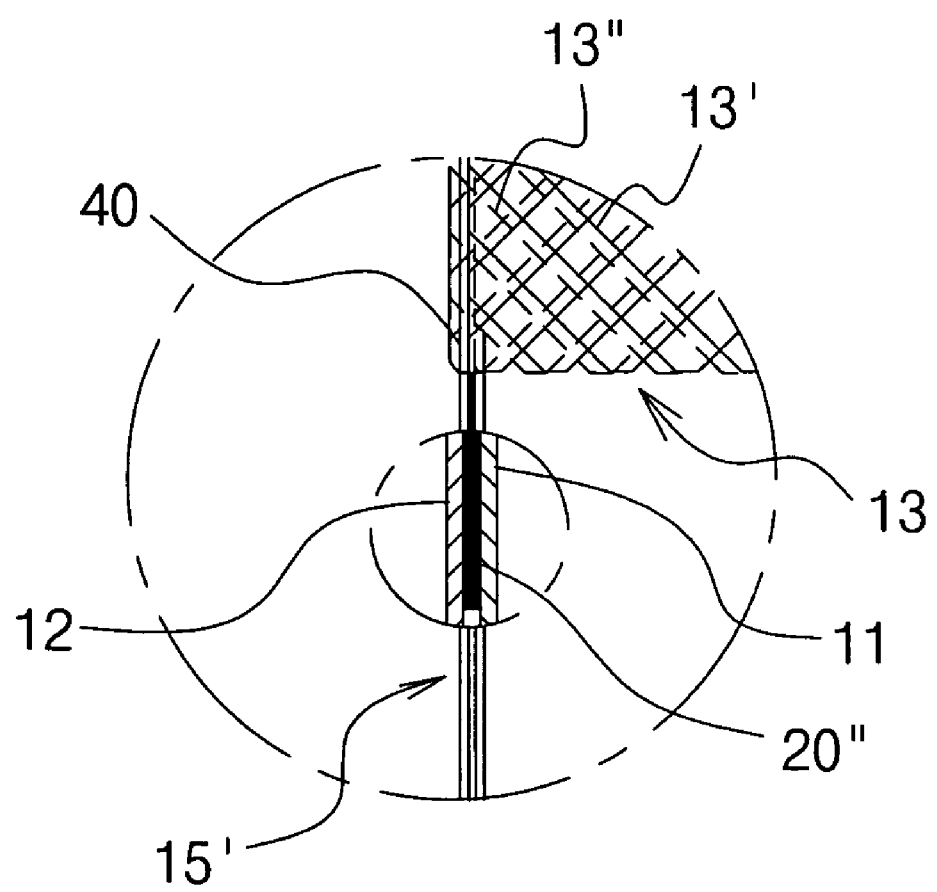
FIG. 8 is a sectional view illustrating a part of the esophageal stent of FIG. 7.
Figure 9:
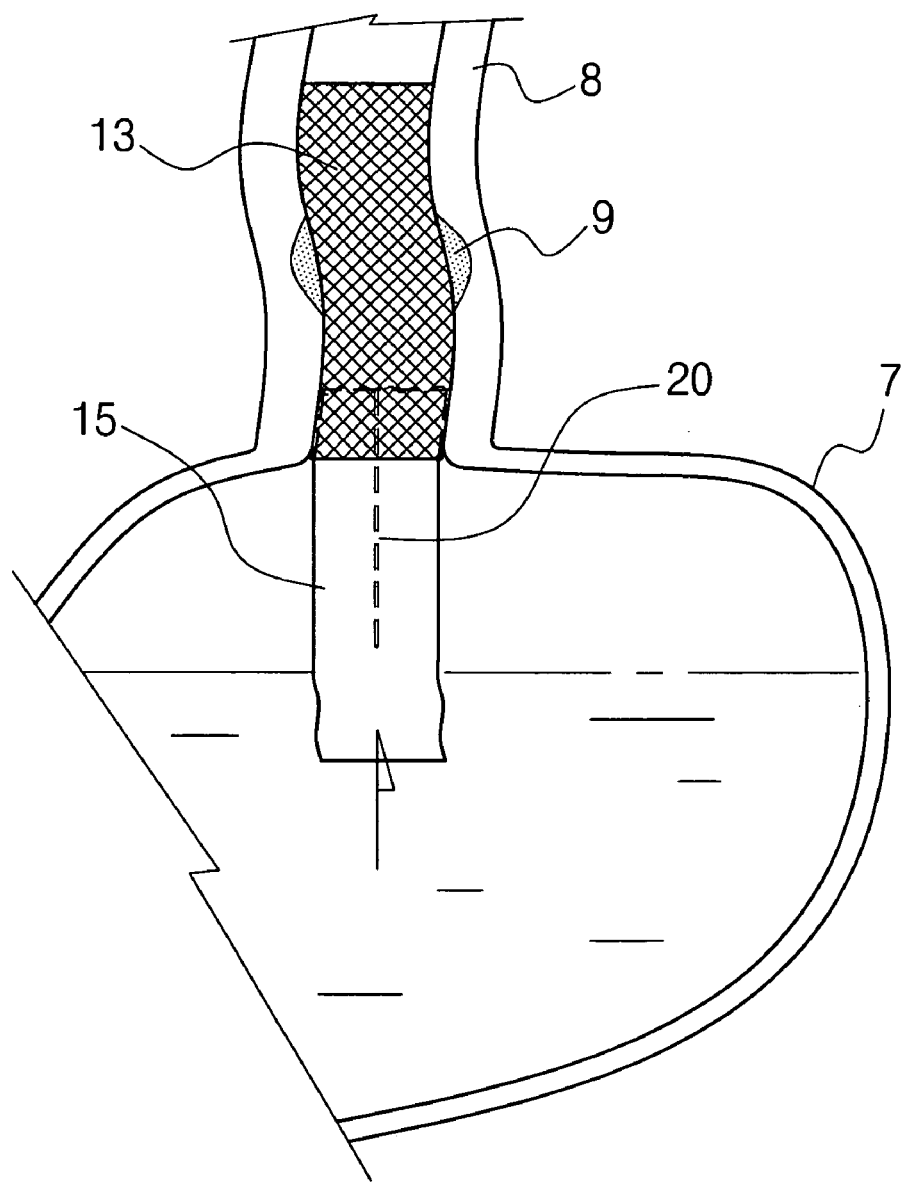
FIG. 9 is a view illustrating the stent of the present invention which is placed in the lower end of the gullet, which communicates with the stomach.

As shown in FIG. 8, using a stent insertion device (not. shown), the esophageal stent is inserted into and placed at a lesioned part 9 of the lower end of the gullet 8, at which the gullet 8 communicates with the stomach 7 where the esophageal sphincter is located. Therefore, the stent pushes the wall of the stenosed lesioned part outwards in radial directions and enlarges the size of the passage of the stenosed lesioned part, thus making swallowing easier.

To place the esophageal stent at the lesioned part of the stenosed gullet, an operator primarily shrinks the stent body 13 and the reverse flow prevention tube 15 so as to reduce the volume of the stent, installs the shrunken stent in the stent insertion device, and inserts the stent into the stenosed lesioned part 9 of the gullet 8 using the insertion device. After the stent reaches the stenosed part 9 of the gullet 8, the stent is pushed so that the stent body 13, fabricated from shape-memory alloy wires, is separated from the insertion device and elastically expands and restores its original shape, thus pushing the wall of the stenosed part 9 outwards in radial directions, thereby enlarging the size of the passage of the stenosed part 9. Simultaneously, the reverse flow prevention tube 15 is expanded by the elastic core 20, thus restoring its original shape along with the stent body 13 and maintaining a desired tubular shape.

In the above state, the reverse flow prevention tube 15, coupled to the lower end of the stent body 13, is placed in the stomach 7.

The esophageal stent, placed at the stenosed lesioned part 9 of the gullet 8 as described above, enlarges the size of the passage of the stenosed part 9 of the gullet 8, so that food can smoothly and safely flow from the mouth down to the stomach 7 through the stent body 13 and the flexible tube 15.

Furthermore, because the core 20 extends from the upper end of the flexible reverse flow prevention tube 15 a distance of at least half of the length (1) of the flexible tube 15, the tube 15 maintains a cylindrical tubular shape within a part having the core 20 and maintains a flexible state within the other part which does not have the core 20.

Therefore, although the part of the flexible tube 15, which does not have the core 20, moves within the stomach 7 due to movement of food within the stomach 7, the moving part of the tube 15 does not come into contact with or stimulate the inner surface of the stomach 7. Thus, the flexible tube 15 of the stent does not cause a patient pain.

Furthermore, because the upper part of the flexible reverse flow prevention tube 15 is supported by the core 20 and only the lower part of the tube 15 is flexible, even if the patient clears his/her throat or is nauseous, thus causing pressure to act in the reverse flow prevention tube 15 and causing the reverse flow of gastric contents from the stomach 7 due to the pressure, the tube 15 is prevented from being inverted into the hollow stent body 13. Therefore, the esophageal stent of this invention completely prevents the reverse flow of food from the stomach 7.

Figure 5:
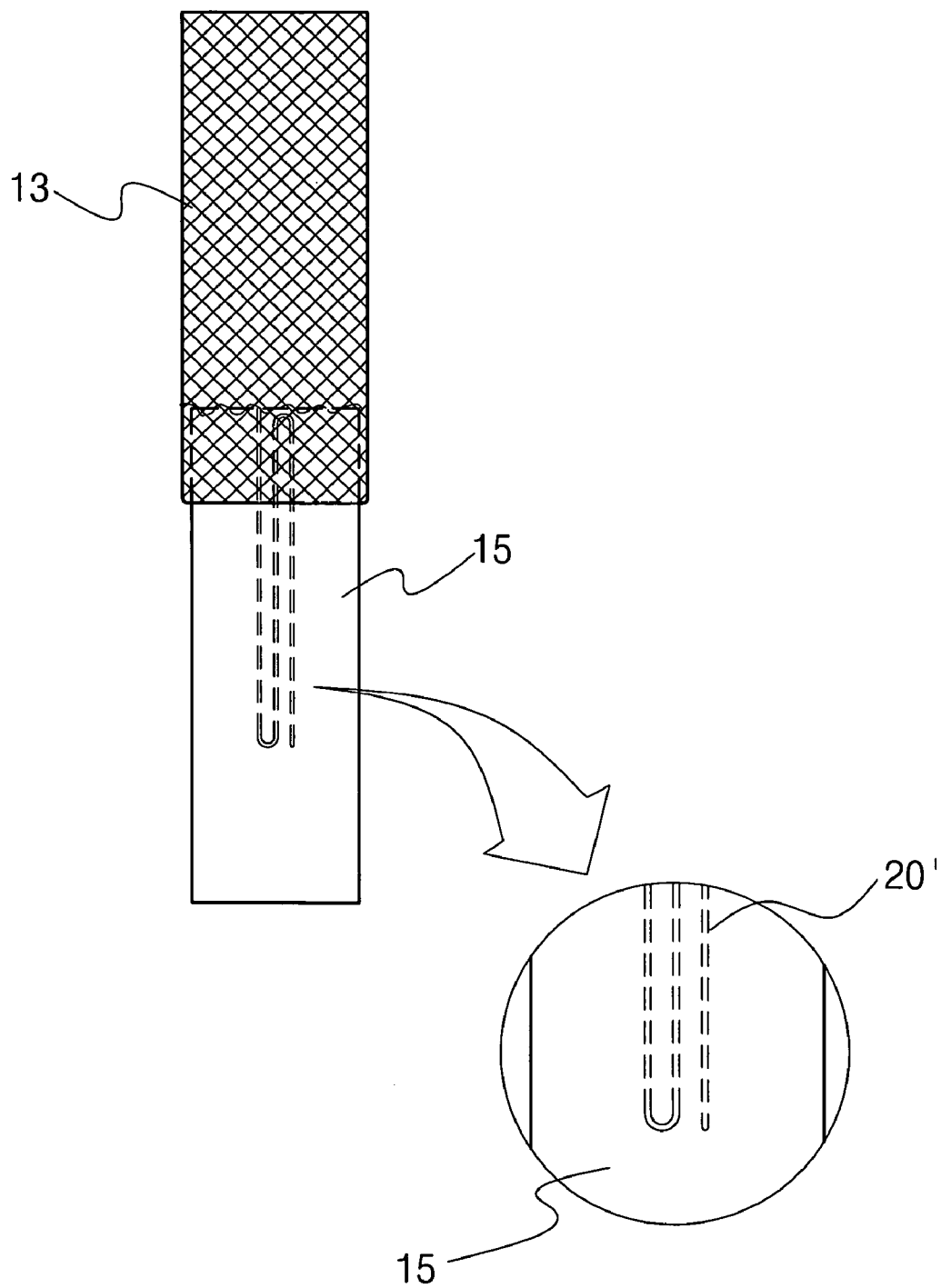
FIG. 5 is a front view illustrating the construction of an esophageal stent according to a second embodiment of the present invention.

FIG. 5 is a front view illustrating the construction of an esophageal stent according to a second embodiment of the present invention. As shown in the drawing, the esophageal stent according to the second embodiment comprises at least one core 20' which is bent to form a zigzag pattern and is placed between the adhered inside and outside membranes 11 and 12 of the flexible reverse flow prevention tube 15.

When the esophageal stent of the second embodiment is compared with the stent of FIGS. 3 and 4, the core 20' is bent longitudinally to form a zigzag pattern and is placed between the adhered inside and outside membranes 11 and 12 of the flexible reverse flow prevention tube 15, so that the volume of the core 20' can be reduced along with the flexible tube 15. Furthermore, the zigzagged core 20' increases an elastic force that opens the flexible tube 15 outwards in radial directions and enlarges an effective range on the tube 15 on which the elastic force acts. Thus, the zigzagged core 20' of the second embodiment supports the flexible tube 15 more efficiently when compared with the core 20 of the first embodiment.

Figure 6:
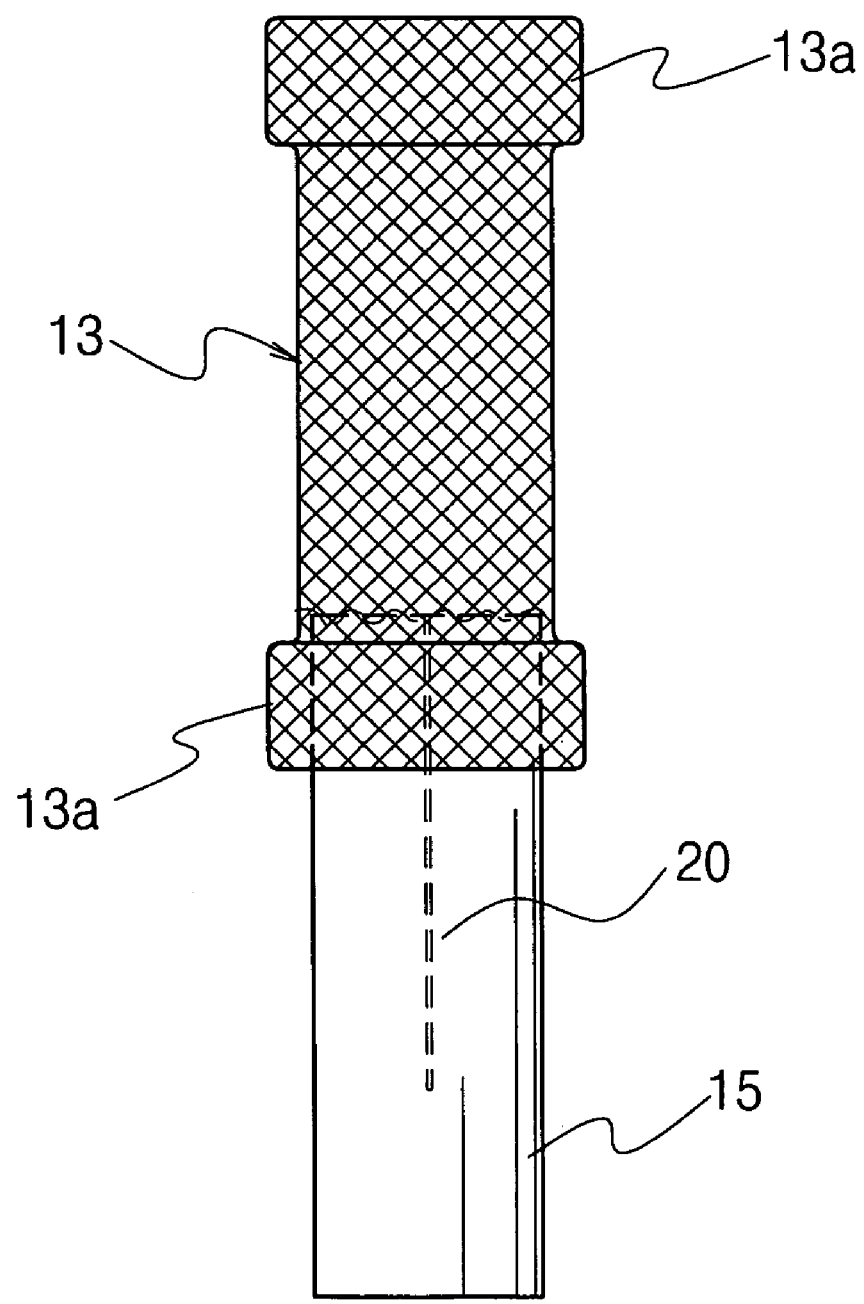
FIG. 6 is a front view illustrating the construction of an esophageal stent according to a third embodiment of the present invention.

The flexible reverse flow prevention tube 15 having the core 20 or 20' according to the present invention may be used with an esophageal stent body 13 having a simple cylindrical shape, as shown in FIGS. 3, 4 and 5. However, it should be understood that the flexible tube 15 having the core 20 or 20' may be used with an esophageal stent body 13 according to the third embodiment of the present invention, in which an enlarged diameter part 13a is provided on each end of the stent body 13 so that the stent body 13 can be caught and reliably maintained in a designated part of the gullet, as shown in FIG. 6.

Furthermore, the flexible reverse flow prevention tube 15 having the core 20 or 20' may be used with another type of esophageal stent body having a coating layer or an artificial membrane to prevent food from coming into contact with a lesioned part of the gullet and from causing pain to a patient while the food flows through the gullet, according to the fourth embodiment of the present invention.

Figure 7:
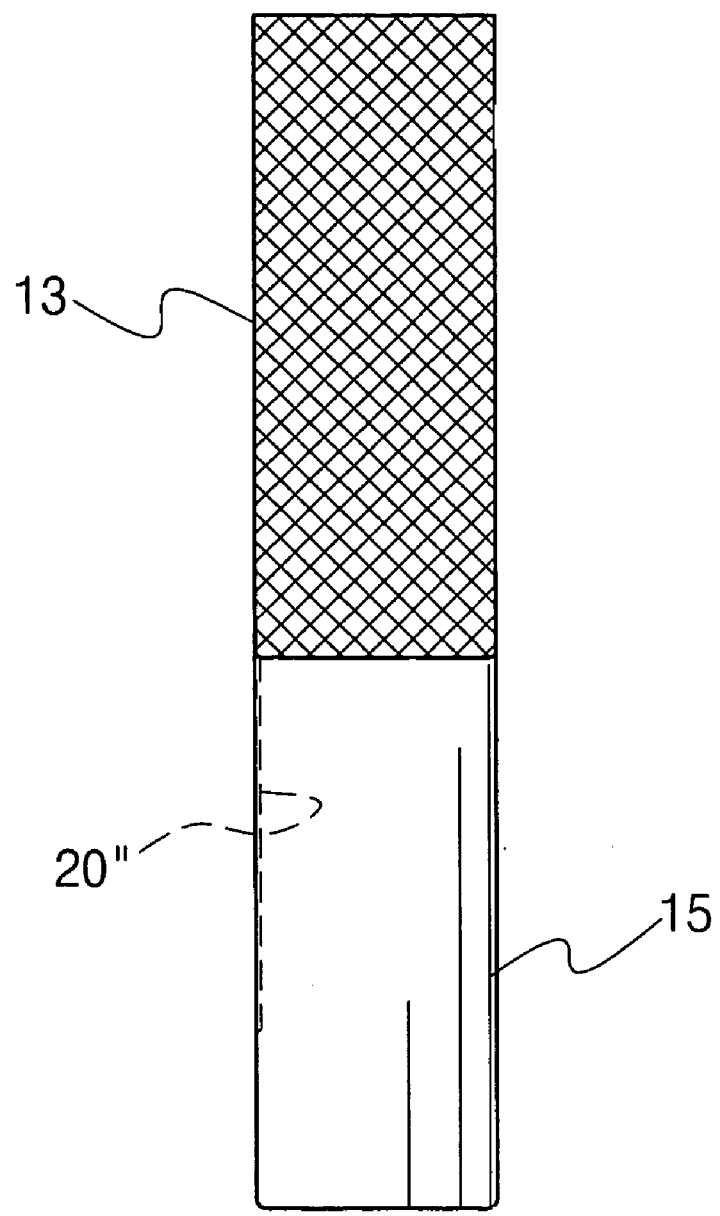
FIG. 7 is a front view illustrating the construction of an esophageal stent according to a fourth embodiment of the present invention.

The esophageal stent, including a stent body 13 having an artificial membrane 40 and a flexible reverse flow prevention tube 15' according to the fourth embodiment of the present invention, is configured as follows. As shown in FIGS. 7 and 8, the esophageal stent comprises an inside stent body 13' and an outside stent body 13", each having a hollow cylindrical mesh structure fabricated by weaving superelastic shape-memory alloy wires, with an artificial membrane 40 placed between the inside and outside stent bodies 13' and 13".

The esophageal stent of the fourth embodiment further comprises a reverse flow prevention tube 15' which is provided by extending the lower end of the artificial membrane 40 downwards from the lower ends of the inside and outside stent bodies 13' and 13" a predetermined distance, inwardly and inversely folding the lower end of the artificial membrane 40 so as to form a twofold structure, and adhering the folds of the membrane 40 to each other.

The stent further includes a core 20" which integrally extends downwards from the lower end of the inside stent body 13' and is placed between the adhered folds of the reverse flow prevention tube 15'.

In the fourth embodiment, the core 20" preferably extends from the upper end of the flexible reverse flow prevention tube 15' a distance of at least half of the length (1) of the flexible tube 15' in the same manner as that described for the first embodiment.

The esophageal stent having the flexible tube 15' and the core 20" according to the fourth embodiment may be inserted into and placed at a lesioned stenosed part of the gullet in the same manner as that described for the first embodiment, and provides the same operational effect as described for the first embodiment.

Unlike the first, second and third embodiments of the present invention, the esophageal stent according to the fourth embodiment is configured such that the flexible reverse flow prevention tube 15' is provided by extending the lower end of the artificial membrane 40, preferably made of PTFE which is benign to the human body, downwards from the lower ends of the inside and outside stent bodies 13' and 13" a predetermined distance, inwardly and inversely folding the lower end of the artificial membrane 40 so as to form a twofold structure. Furthermore, the core 20" integrally extends downwards from the lower end of the inside stent body 13' and is placed between the adhered folds of the reverse flow prevention tube 15', without forming a separate core placed in the tube 15'.

In the above description, the stent of the present invention has been described to be used in the gullet, however, it should be understood that the stent may be inserted into and placed in the bile duct as well as the gullet.

As described above, the present invention provides an esophageal stent comprising a stent body and a flexible reverse flow prevention tube coupled to the lower end of the stent body and preventing the reverse flow of gastric contents, wherein the flexible reverse flow prevention tube comprises inside and outside membranes adhered to each other, thus having a twofold structure with at least one elastic core longitudinally inserted into the adhered inside and outside membranes and placed between the membranes while the core extends from the upper end toward the lower end of the flexible tube. Thus, the flexible reverse flow prevention tube can be prevented from being inverted into the hollow stent body, thus preventing gastric contents from undesirably flowing reversely from the stomach through the inverted flexible tube. Furthermore, the flexible tube of the esophageal stent does not cause a patient pain or discomfort due to frictional contact of the tube with the inner surface of the stomach when the tube moves in the stomach. Thus, the esophageal stent of this invention has maximized operational reliability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:
1. An esophageal stent, comprising:
a stent body having a hollow cylindrical mesh structure formed from interweaved superelastic shape-memory alloy wires;
a reverse flow prevention tube, having a substantially cylindrical tubular shape, being coupled to a lower end of the stent body, the reverse flow prevention tube comprising an inside membrane and an outside membrane adhered to each other for forming a flexible twofold structure; and at least one core being longitudinally disposed between the inside and outside membranes, said core extending only a partial distance from an upper end toward a lower end of the reverse flow prevention tube thereby maintaining the substantially cylindrical tubular shape of the reverse flow prevention tube over said partial distance and maintaining a flexible state within a remainder of the reverse flow prevention tube between a lower end of the at least one core and the lower end of the reverse flow prevention tube where the at least one core is not present.

2. The esophageal stent of claim 1, wherein the inside and outside membranes of the flexible reverse flow prevention tube are formed by a single membrane, said single membrane being folded such that a lower end of the single membrane is brought upward to an upper end of said single membrane for forming said inside and outside membranes.

3. The esophageal stent of claim 1, wherein said partial distance over which the at least one core extends is at least half of a length of the reverse flow prevention tube.

4. The esophageal stent of claim 1, wherein the at least one core is bent longitudinally to form a zigzag pattern.

5. The esophageal stent of claim 1, wherein said stent body includes a coating layer or an artificial membrane being disposed thereon which prevents food which passes trough the stent body form coming in contact with a lesioned part of a gullet.

6. The esophageal stent of claim 1, wherein a terminal end portion of said reverse flow prevention tube is coupled to said lower end of the stent body.

7. The esophageal stent of claim 1, wherein said at least one core operates to prevent said reverse flow prevention tube from becoming inverted into the stent body.

8. An esophageal stent, comprising:
an inside stent body and an outside stent body, each having a hollow cylindrical mesh structure formed from interweaved superelastic shape-memory alloy wires; and
an artificial membrane, a portion of which is disposed between the inside and outside stent bodies;
a reverse flow prevention tube being defined by an other portion of the artificial membrane which extends by a predetermined distance downwardly from lower ends of the inside and outside stent bodies, said reverse flow prevention tube including a twofold membrane structure comprised of a first portion of the membrane folded along a fold and extended inwardly and inversely relative to a second portion of said membrane such that said first and second portions of said membrane overlap one another, said first and second portions of said membrane being adhered one to another; and
at least one core integrally extending downwardly from a lower end of the inside stent body and being disposed between the portions of the artificial members of the reverse flow prevention tube, said at least one core extending only a partial distance from the lower end of the inside stent body to said fold thereby maintaining a substantially cylindrical tubular shape of the reverse flow prevention tube over said partial distance and maintaining a flexible state within a remainder of the reverse flow prevention tube between a lower end of the at least one core and the lower end of the reverse flow prevention tube where the at least one core is not present.

9. The esophageal stent of claim 8, wherein said partial distance over which the at least one core extends is at least half of a length of the reverse flow prevention tube.

10. The esophageal stent of claim 8, wherein said at least one core operates to prevent said reverse flow prevention tube from becoming inverted into the inside stent body or the outside stent body.

11. An esophageal stent, comprising:
a stent body having a hollow mesh structure formed from interweaved superelastic shape-memory alloy wires, said stent body having a shape defined, by a cylindrical central portion and enlarged diameter parts on both ends of the stent body;
a reverse flow prevention tube, having a substantially cylindrical tubular shape, being coupled to a lower end of the stent body, the reverse flow prevention tube comprising an inside membrane and an outside membrane adhered to each other for forming a flexible twofold structure; and
at least one core being longitudinally disposed between the inside and outside membranes, said core extending only a partial distance from an upper end toward a lower end of the reverse flow prevention tube thereby maintaining the substantially cylindrical tubular shape of the reverse flow prevention tube over said partial distance and maintaining a flexible state within a remainder of the reverse flow prevention tube between a lower end of the at least one core and the lower end of the reverse flow prevention tube where the at least one core is not present.

12. The esophageal stent of claim 11, wherein said partial distance over which the at least one core extends is at least half of a length of the reverse flow prevention tube.

13. The esophageal stent of claim 11, wherein a terminal end portion of said reverse flow prevention tube is coupled to said lower end of the stent body.

14. The esophageal stent of claim 11, wherein said at least one core operates to prevent said reverse flow prevention tube from becoming inverted into the stent body.

* * * * *